United States Patent
Theodoulou et al.

(10) Patent No.: US 9,512,394 B2
(45) Date of Patent: Dec. 6, 2016

(54) ANAEROBIC DIGESTER SERVICE DEVICE WITH A SEPARATION CURTAIN

(71) Applicant: Anaergia Inc., Burlington (CA)

(72) Inventors: Michael David Theodoulou, Milton (CA); Warren Bruce Lee, Hillsburgh (CA); Juan Carlos Josse, Mission Viejo, CA (US)

(73) Assignee: Anaergia Inc., Burlington (CA)

( * ) Notice: Subject to any disclaimer, the term of this patent is extended or adjusted under 35 U.S.C. 154(b) by 4 days.

(21) Appl. No.: 14/358,574

(22) PCT Filed: Nov. 16, 2012

(86) PCT No.: PCT/CA2012/050821
§ 371 (c)(1),
(2) Date: May 15, 2014

(87) PCT Pub. No.: WO2013/071444
PCT Pub. Date: May 23, 2013

(65) Prior Publication Data
US 2014/0329306 A1    Nov. 6, 2014

Related U.S. Application Data

(60) Provisional application No. 61/561,088, filed on Nov. 17, 2011, provisional application No. 61/595,354, filed on Feb. 6, 2012.

(51) Int. Cl.
*C12M 1/107*    (2006.01)
*C12M 1/00*    (2006.01)
(Continued)

(52) U.S. Cl.
CPC .......... *C12M 23/36* (2013.01); *B01F 7/00733* (2013.01); *C12M 21/04* (2013.01);
(Continued)

(58) Field of Classification Search
CPC ....... C12M 21/04; C12M 23/00; C12M 23/38; C12M 27/06; C12M 23/36; C12M 39/00; C12P 5/023; B01F 7/00733; Y02E 50/343; Y02E 29/49718; Y02E 137/0441; Y02E 137/7043
See application file for complete search history.

(56) References Cited

U.S. PATENT DOCUMENTS

2009/0218279 A1    9/2009  Eichler et al.
2010/0261242 A1*   10/2010 Harvey et al. ......... C12M 21/04
                                                 435/161
2012/0164720 A1*   6/2012  Bierer et al. ........ B01F 7/00733
                                                 435/289.1

FOREIGN PATENT DOCUMENTS

DE        40 15 478 C1    9/1991
DE        197 14 342 C1   10/1998
(Continued)

OTHER PUBLICATIONS

Bierer, Johann, English translation of WO 2010/084003 A3, Jul. 29, 2010.
(Continued)

*Primary Examiner* — Gautam Prakash (57) ABSTRACT

A digester tank has a servicing device that allows access to the interior of the digester tank. The sealing device may have a movable retention wall adapted to resist the pressure of the gas inside the digester by one or more of a) increasing the bending resistance of the retention wall, for example by inflating pockets in the wall, b) forcing the lower edge of the retention wall downwards, for example by weight, a mechanical arm or inflating pockets, and c) providing a mechanical structure within the retention wall, for example a non-moving cage-like structure. A sealing device with a fixed wall has a pipe with an isolation valve between the headspace of the tank and the inside of the sealing device.

(Continued)

In operation, a seal may be formed across the separation curtain by raising the level of the liquid contents and closing the isolation valve.

29 Claims, 9 Drawing Sheets

(51) Int. Cl.
  *C12M 1/06*  (2006.01)
  *C12P 5/02*  (2006.01)
  *B01F 7/00*  (2006.01)

(52) U.S. Cl.
  CPC ............ *C12M 23/00* (2013.01); *C12M 23/38* (2013.01); *C12M 27/06* (2013.01); *C12M 39/00* (2013.01); *C12P 5/023* (2013.01); *Y02E 50/343* (2013.01); *Y10T 29/49718* (2015.01); *Y10T 137/0441* (2015.04); *Y10T 137/7043* (2015.04)

(56) References Cited

FOREIGN PATENT DOCUMENTS

| | | |
|---|---|---|
| DE | 199 51 959 A1 | 10/1999 |
| DE | 200 15 808 U1 | 9/2000 |
| DE | 20 2004 004 101 U1 | 9/2004 |
| DE | 20 2007 007 060 U1 | 8/2007 |
| DE | 10 2009 031 177 A1 | 12/2010 |
| EP | 1 717 305 B1 | 9/2007 |
| EP | 2 270 128 A1 | 1/2011 |
| EP | 2 497 822 A1 | 9/2012 |
| WO | 2010084003 A3 | 7/2010 |
| WO | 2013071444 A1 | 5/2013 |

OTHER PUBLICATIONS

Kraemer, Guenter, English translation of DE 4015478 C1, Sep. 12, 1991.
Lehmann, Uwe, English translaiton of DE 199 51 959 A1, Oct. 28, 1999.
Bierer, Johann, English translation of EP 2 270 128, Jan. 5, 2011.
UTS Biogastechnik Gmbh, English language abstract of DE102009031177, published Dec. 30, 2010.
Sattler AG, English language abstract of DE202007007060, published Jul. 26, 2007.
Niiederbacher, Michael, English language abstract of EP2497822, published Sep. 12, 2012.
Partial Supplementary European Search Report dated Jun. 25, 2015, issued in related European Application Serial No. 12849716.1.
Extended European Search Report dated Oct. 5, 2015, issued in related European Application Serial No. 12849716.1.

\* cited by examiner

Prior Art

FIG. 4

Prior Art

ANAEROBIC DIGESTER SERVICE DEVICE WITH A SEPARATION CURTAIN

RELATED APPLICATIONS

This application is a National Stage Entry of International Application No. PCT/CA2012/050821, filed Nov. 16, 2012, which claims the benefit of U.S. provisional application No. 61/561,088 filed on Nov. 17, 2011 and U.S. provisional application No. 61/595,354 filed on Feb. 6, 2012. U.S. provisional application No. 61/561,088 and U.S. provisional application No. 61/595,354 are incorporated by reference.

FIELD

The present invention relates to an anaerobic digester for producing biogas and to a servicing device for an anaerobic digester.

BACKGROUND

An anaerobic digester, alternatively called a fermenter or biogas plant, may have a tank in which a substrate is digested, or fermented, and biogas is produced. The tank is typically closed at the top with a cover. The tank contains a mixture of solids and liquids, also referred to as the digestate, liquid contents, fermentation section, or sludge, which is being digested and producing biogas. Biogas collects in the head space of the tank, alternatively called a gas section, above the liquid contents. An agitator or mixer is typically provided within the tank to agitate, stir, mix, or at least partially homogenize the liquid contents to encourage biogas production and digestion.

The agitators, however, may require inspection, maintenance or repair at some times. Agitators may be supported on a generally vertical holding rod or otherwise made movable between the liquid contents and the gas section. However, access to the agitator still needs to be provided through the cover.

German patent application DE 199 51 959 A1 describes a digester having a flat concrete cover. A rectangular maintenance shaft extends downwards from the cover into the liquids portion. An agitator can be lifted into the maintenance shaft. A hatch through the cover allows access to the agitator in the maintenance shaft.

European Patent Number EP 1 717 305 B1 describes a service pit that is mounted on a frame connected to the inside wall of a digester tank. The sides of the service pit are sealed to a dome shaped tank cover. An agitator can be moved upwards into the service pit for servicing. Part of the service pit extends upwards above the cover. A vertical door in the front of the service pit above the cover can be opened to access the agitator. International Publication Number WO 2010/084003 describes a variation of this design in which the service pit is mounted to a frame connected to the outside of the tank, to an extension of the wall of the tank, or to the ground outside of the tank.

European Patent Number 2 270 128 B1 describes a servicing device for a digester with a movable sealing device. The sealing device has a gas retention wall made of a flexible material. The sealing device can be raised into an inoperative position or lowered into a sealing position. In the inoperative position, the sealing device does not interfere with the operation of the digester. In the sealing position, the lower edge of the sealing device is located on or in the liquid contents of the digester and separates the inside of the servicing device from the gas section of the digester. While the sealing device is in the sealing position, an agitator can be moved upwards into the servicing device. A door in the servicing device is opened and, after the biogas escapes from the servicing device, the agitator can be serviced.

INTRODUCTION

A servicing device, alternatively called a service device, a service box, or a service pit, generally as described in European Patent Number 2 270 128 B1 is commercially available from UTS Biogastechnik and Anaergia Inc. These devices are successful products. However, there is still room for improvements, alternative devices, or devices that include different features that may be useful in some circumstances. For example, the inventors have observed that in high pressure digesters the biogas may force parts of the gas retention wall inwards. In some cases, this deflection lifts the lower edge of the sealing device and causes a leak, or interferes with moving the agitator into the servicing device.

A service device, a combination of a service device and a digester tank, and a method of servicing a digester, are described in this specification. The service device is supported on the tank, or on the ground near the tank. The outside of the service device is sealed to a cover of the tank. The inside of the service device can be put in fluid communication with a gas section of the tank or separated from the gas section of the tank. A hatch in the service device allows access to the inside of the tank from outside of the service device.

In some examples, a service device has a sealing device which can be moved between an inoperative position and a sealing position. The sealing device may have a retention wall comprising a flexible material. Optionally, means are provided to increase the ability of the sealing device to resist biogas pressure while the service device is open to the atmosphere. The means may include one or more of: a) increasing the bending resistance of the retention wall, for example by inflating pockets in the wall, b) forcing the lower edge of the retention wall downwards, for example with a mechanical arm, piston or inflatable pockets, and c) providing a mechanical supporting structure within the retention wall, for example a non-moving cage-like structure. These options may be used alone or in any possible combination. Optionally, means are provided for moving the sealing device. For example, the sealing device may be moved by inflatable pockets, by pistons, or by springs. Optionally, the sealing device may be biased upwards, but selectively forced downwards.

In some examples, a service device includes a fixed separation curtain, alternatively called a shaft, which extends downwards from a tank cover towards the liquid contents of a tank. The servicing device also includes a pipe that provides fluid communication between the gas section and the inside of the servicing device. The pipe can be selectively closed to prevent this communication. Preferably, the pipe extends inwards from a port in the separation curtain and then upwards within the service device. Once above the cover, the pipe may pass through a wall of the service device and then return to a port in the service device. A shut off valve may be located in the portion of pipe outside of the service device and above the cover. Optionally, the service device may have a purge line with a valve and a vent with a valve. Optionally, the service device may have a biogas outlet. Optionally, a digester may have two or more service devices.

In a method of operating a digester with a service device having a fixed separation curtain, the surface of the liquid contents is made high enough, at least when servicing is required, to form a seal with the bottom of the separation curtain. The vent pipe is closed, which isolates the gas section from the inside of the service device. Optionally, the service device may be purged of biogas. In a digester with more than one service device, biogas may be withdrawn from a second service device while a first service device is isolated by leaving the pipe of the second device open. After inspecting or servicing the digester, the vent pipe is re-opened. Optionally, when no service device is in use the liquid contents may be lowered or allowed to drop to below the bottom of the separation curtain.

Optionally, the servicing device may be combined with other features. For example, the servicing device may be used to hold an upper end of an agitator supporting rod. The servicing device may have an arm, preferably operable from outside of the servicing device, for rotating the supporting rod. The servicing device may have a gas outlet for extracting biogas from the digester. The servicing device may have a viewing port. The servicing device may have a platform to support a person working on the digester. The servicing device may have a door to allow a person to have access to the inside of the servicing device. The servicing device may have means for raising or lowering an agitator on the supporting rod.

DETAILED DESCRIPTION

FIGS. 1 to 5 show a biogas plant 1 with a servicing device 2. The biogas plant 1 illustrated in side view in FIG. 1 comprises a fermenter tank 4. The interior space 7 of the fermenter tank is divided into a lower fermentation section 7 and an upper gas section 6. A fermentable or otherwise digestible substrate, to be converted in part into biogas, is located in the fermentation section 5. Biogas collects in a gas section 6.

Figure 1:
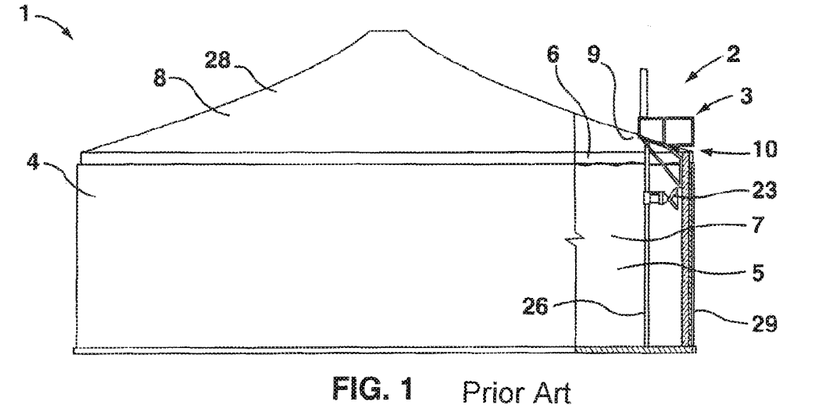
FIG. 1 is a schematic side view of a digester with a partial cross section.

The fermenter tank 4 comprises a tank wall 29 and a tank cover 8, alternatively called a gas closing wall. The tank cover 8 in the example of FIG. 1 is a flexible top sheeting 28. In other examples, the tank cover 8 could be a flat or domed solid cover made of plastic, metal or concrete; a double walled membrane; or another structure.

For agitating the substrate in the fermentation section 5 and for promoting the digestion process, at least one agitator 23 is provided. The agitator 23 is mounted on a holding rod 26 extending from the bottom 27 of the fermenter tank 4 preferably at least as far as the tank cover 8.

The fermenter tank 4 is provided with at least one servicing device 2. An upper part of the servicing device 2, which extends above the tank cover 8 and optionally also extends below the tank cover 8, is referred to as a servicing unit 3. A lower part of the sealing device 2, which is attached to the bottom of the servicing unit 3, is referred to as a sealing device 9.

The servicing device 2 in the example of FIG. 1 is supported on a carrying console 14, alternatively called a frame, attached to the inside of the tank wall 29. Alternatively, the servicing device 2 may be supported on a frame attached to the outside of the tank wall, or on a frame supported on the ground near the fermenter tank 4.

The servicing unit 3 comprises an optional platform 34 for a person to stay on while installing, inspecting or servicing part of the biogas plant 1, particularly the agitator 23. The outside of the servicing device 2 is connected to the tank cover 8 so as to be gas-tight or at least nearly gas tight. A hatch is not visible in the Figures but is located in the vertical wall of the servicing unit 3 in front of the platform 34.

Figure 2:
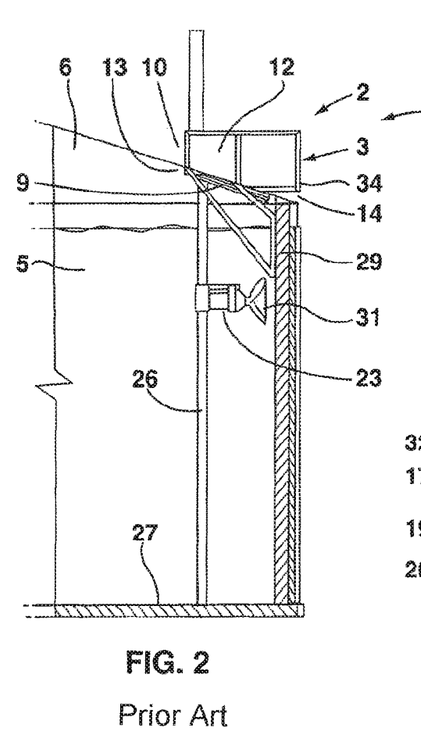
FIG. 2 is an enlarged illustration of a service device of the digester in FIG. 1.

In FIGS. 1 and 2, the sealing device 9 is in an inoperative (non-sealing) position 10 in which a gas retention wall 15 of the sealing device 9 is disposed and contracted against an attachment frame 13. The attachment frame 13 holds the top of the sealing device 9 and allows it to be attached to the servicing unit 3. In the inoperative position 10, the sealing device 9 requires little space. This position is provided for normal operation of the biogas plant 1 wherein the agitator 23 agitates or mixes the substrate in the fermentation section 5 while the biogas produced collects in the gas section 6.

Figure 3:
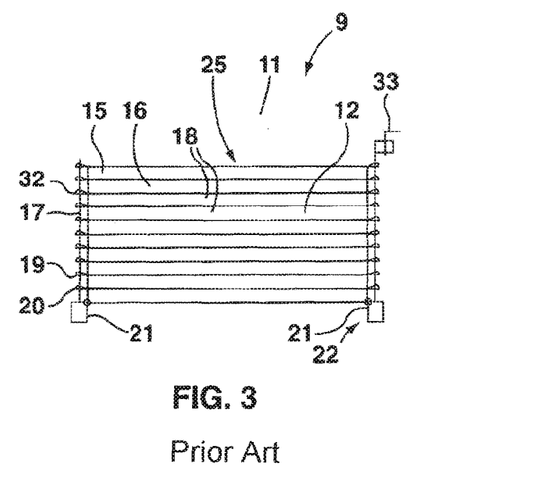
FIG. 3 is a schematic illustration of a sealing device of the service device in FIG. 2.
Figure 4:
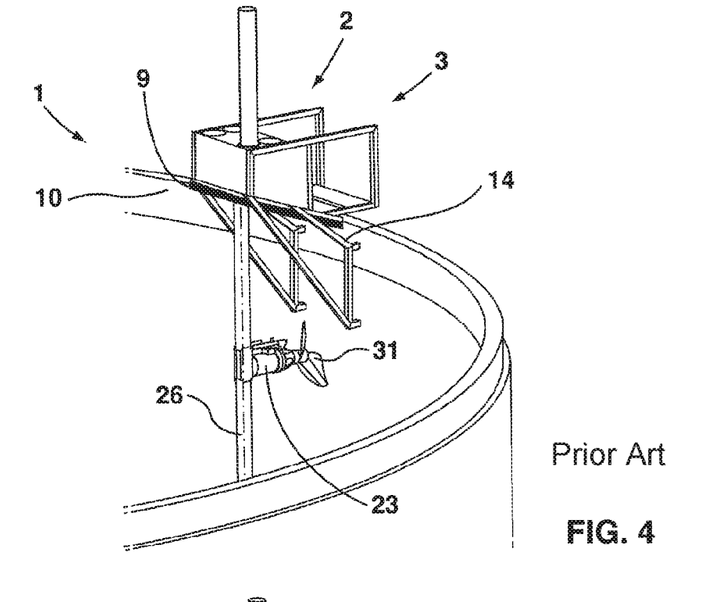
FIG. 4 is a schematic, enlarged view of the service device of FIG. 1 in an inoperative (non-sealing) position.

The gas retention wall 15 is configured as a series of bellows 16. The gas retention wall 15 can be transferred from the position illustrated in FIG. 2 to a telescoped position, alternatively called the sealing position 11, illustrated in FIG. 3. In the example of FIG. 3, flexible guide members 17 configured as ropes are lowered via a crank mechanism 33 and the dead weight of the sealing device 9 or optional additional weights 21 cause the retention wall 15 to descend. The retention wall 15 may be spread out by mounting units 18, for example rigid wire frames, located on the retention wall at specified intervals. The retention wall 15 is connected with the guide member 17 via attachment eyelets 32.

When the guide member 17 is lowered, the weight of the gas separation wall 15 or the additional weights 21 cause the gas retention wall 15 to lower at least until the gas retention wall 15 reaches the surface of the fermentation section 5. The gas retention wall is preferably also partially immersed in the fermentation section 5. This separates the inside 12 of the servicing device 2 from the gas section 6.

In the sealing position 11, maintenance can be performed. The agitator 23 may be rotated by turning the holding rod 26 to align the agitator 23 with the servicing device 2. Optionally, the agitator 23 may be pivoted upwards to help it fit inside the gas retention wall 15. The agitator 23 is raised on the holding rod 26, for example by lifting a cable attached to the agitator 23, until it is located above the fermentation section 5 on the inside 12 of the servicing device 2.

In the example of FIGS. 1 to 5, the agitator 23 may be raised above the tank cover 8 until it is located within the servicing unit 3. Then the hatch in the front of the servicing unit 3 may be opened. After allowing any biogas still present in the servicing unit 3 to escape, the agitator 23 is accessible for inspection or maintenance.

In an alternative configuration, the servicing unit 3 does not extend to form a box or dome above the tank cover 8. Instead, a sloped or horizontal hatch is provided around the elevation of the tank cover 8. With the hatch open, the agitator 23 can be raised to near or above the tank cover 8 and maintenance can be done on the agitator 23 by reaching into the fermenter tank 4 or in the open air above the tank cover 8.

FIG. 4 again shows the sealing device 9 in the inoperative position 10 and the biogas plant 1 normal operation. To allow a better view, the top cover 8 is illustrated as if it were transparent to offer a view into the interior of the fermenter tank 4.

Figure 5:
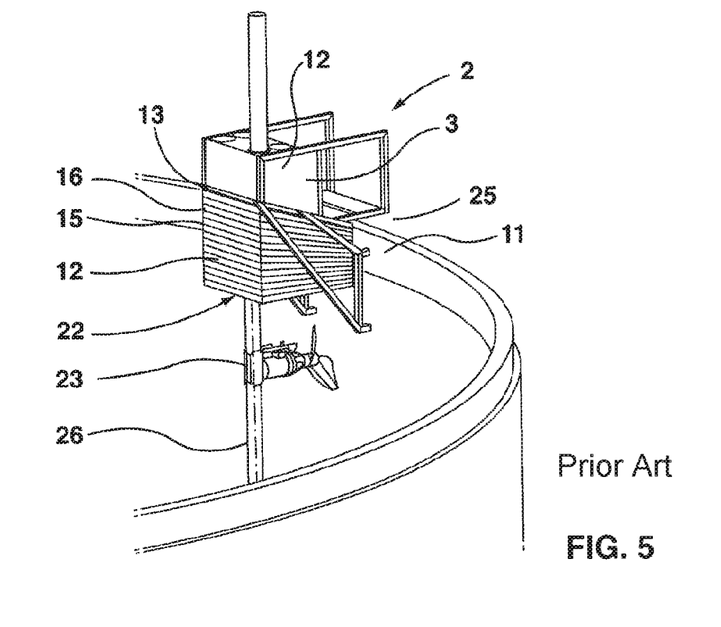
FIG. 5 an illustration of the service device of FIG. 1 in a sealing position.

FIG. 5 shows the sealing position 11 in which the top 25 of the sealing device is separated from the bottom 22 of the sealing device 9 and maintenance may be performed. The retention wall 15 of the sealing device 9 which serves as a gas curtain has been lowered as far as the level of the fermentation section 5.

The description above is similar to that provided in U.S. patent application Ser. No. 12/977,634 is incorporated herein by reference. International Publication WO 2010/084003 A3 is also incorporated herein by reference. That international publication describes a support frame for a servicing device that attaches to the outside of the tank wall. That support frame may be used to hold any of the servicing devices described in this specification as well. The description above of the servicing device 2 applies, unless stated otherwise, to the second to fourth servicing devices which will be described below. Aspects of the servicing device 2 may also be used in combination with the fifth servicing device.

Figure 6:
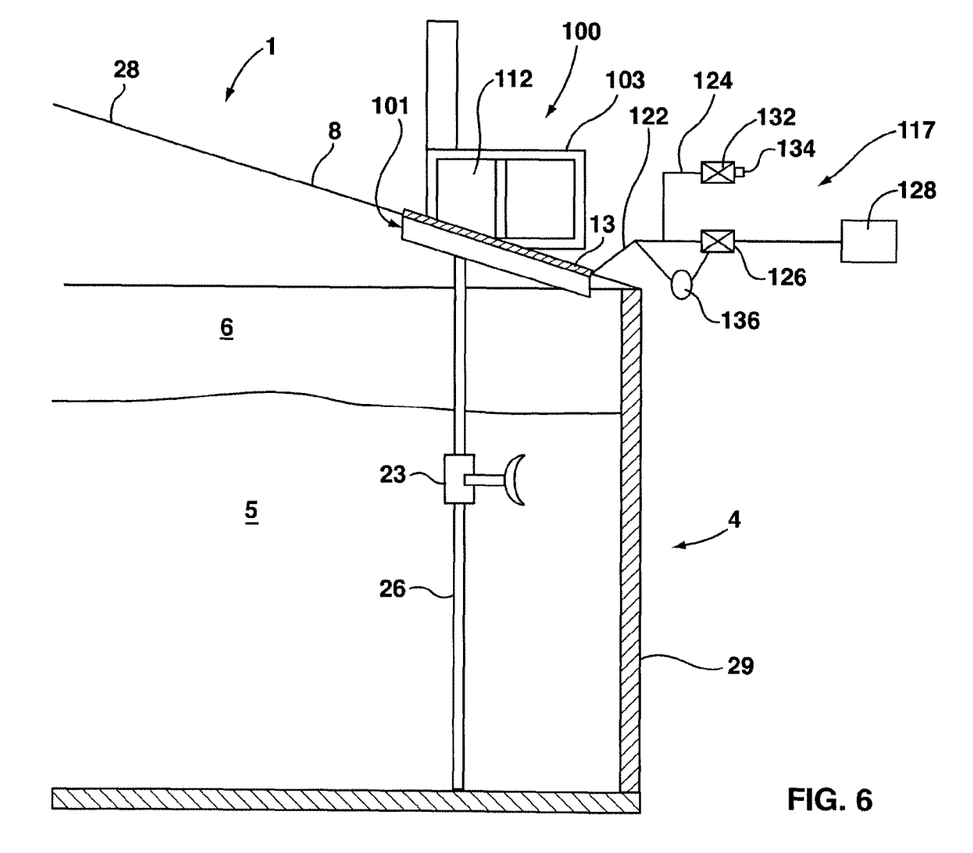
FIG. 6 is a schematic illustration of a second service device in the inoperative position.
Figure 7:
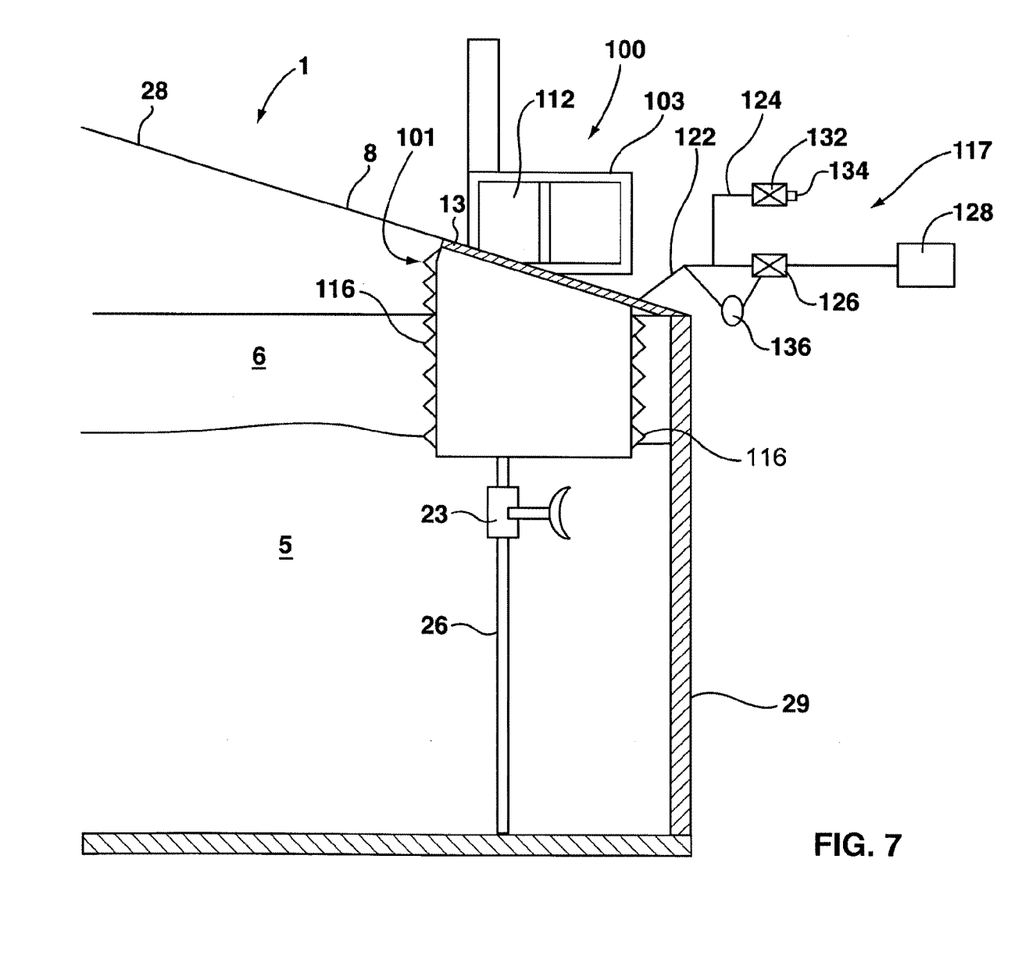
FIG. 7 is a schematic illustration of the second service device in the operative position.

FIGS. 6 and 7 show a second servicing device 100. The second servicing device 100 comprises a second servicing unit 103, a servicing section 112, an inflatable curtain 101 and a control system 117. The inflatable curtain 101 is configured to such that is tends towards an extended position, as shown in FIG. 7, when it is full of compressed air. However, the inflatable curtain 101 can be collapsed, as shown in FIG. 6, when not full of compressed air. In this way, the second servicing device 100 can move between an inoperative position and a sealing position to allow servicing of the agitator 23. While the inflatable curtain 101 is in the inoperative position, biogas is withdrawn from the gas section 6 through the stack shown at the top of the servicing device 2.

The second servicing device 100 includes a second servicing unit 103 that is similar to the servicing unit 3 described above. The servicing section 112 is an enclosed box portion of the second servicing unit 103. The second servicing unit 103 is supported by a carrying console 14 on the tank wall 29. The second servicing unit 103 is connected with the top sheeting 28, or the top cover 8, in a gas-tight manner to prevent the escape of biogas from the gas section 6. The second servicing unit 103 includes a platform 34 and the servicing section 112. The platform 34 can support a person to perform maintenance operations on the agitator 23 when the agitator device 23 is inside the servicing section 112. The servicing section 112 extends across the gas-tight connection of the second service unit 103 to the tank cover 8 and into the gas section 6 of the fermenter tank 4. When a hatch in the front wall of the servicing section 112 is closed, there is no fluid communication between the gas section 6 and the atmosphere through the second servicing device 100. When the servicing section 112 is open, there is communication from the gas section 6 to outside of the fermenter tank 4. During normal operations of the biogas plant 1, the hatch in the service section 112 is closed to prevent the escape of the produced biogas from the gas section 6.

FIG. 6 shows the second servicing device 100 in the inoperative position. The inflatable curtain 101 is shown attached to, and compressed against, an attachment frame 13.

FIG. 7 shows the second servicing device 100 in the sealing position. The inflatable curtain 101 is shown attached to the attachment frame 13 and extending into the fermentation section 5.

Figure 8:
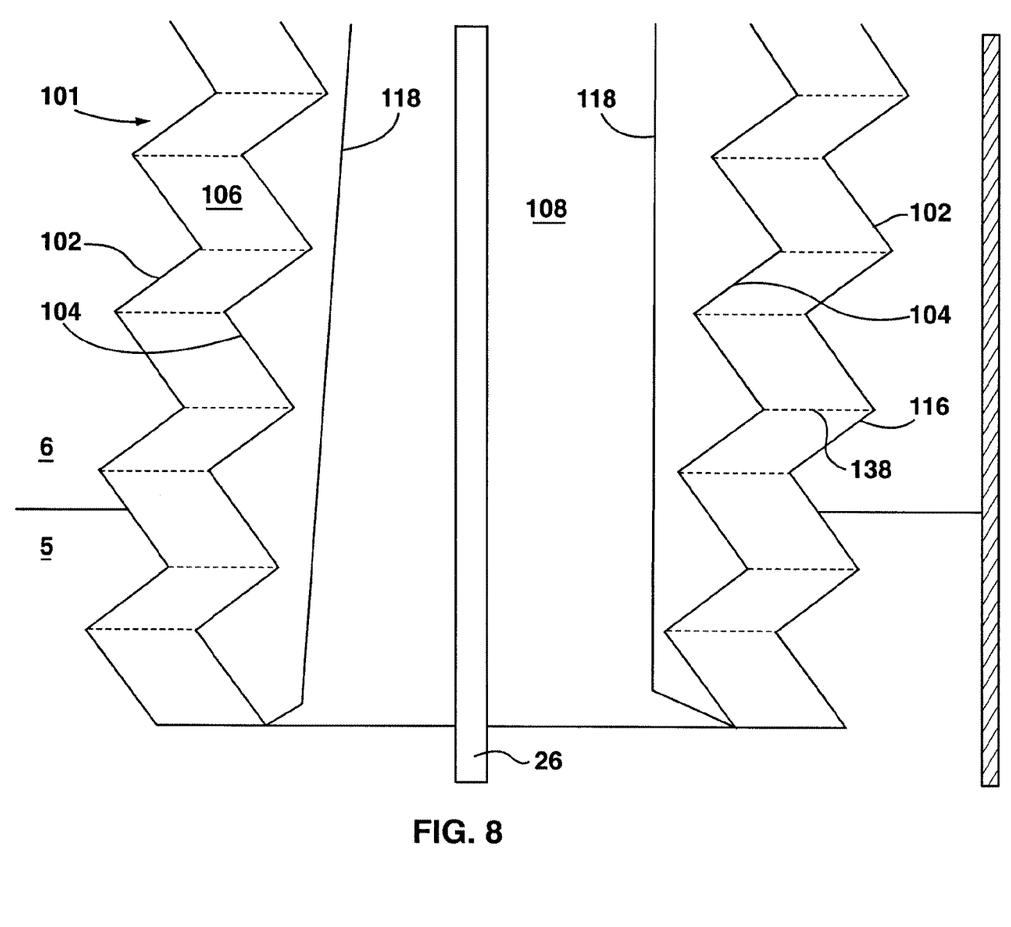
FIG. 8 is a cross-sectional, schematic illustration of the second service device in the operative position.

As shown in FIG. 8, the inflatable curtain 101 includes an outer wall 102 and an inner wall 104. The walls 102, 104 may be made, for example, of molded rubber, rubberized or coated fabric, or flexible plastic sheets. The outer wall 102 and the inner wall 104 form an enclosed service space 108 that encloses a portion of the holding rod 26. The enclosed service space 108 is in fluid communication with the service section 112. The agitator 23 to move along the holding rod 26 through the enclosed service space 108 and into the service section 112. Optionally, the inflatable curtain 101 can be made of a pliable material, for example a flexible plastic or rubber impregnated fabric, which will not corrode or degrade within the environment of the biogas plant 1. The inflatable curtain 101 can also be molded to include creases 116 in the outer and inner walls 102, 104. The creases 116 help the inflatable curtain 101 fold while in the inoperative position and extend while in the sealing position.

The outer and inner walls 102, 104 are spaced apart and closed at the top and the bottom edges. The outer and inner walls 102, 104 define a sealed internal space 106 of the inflatable curtain 101. When the inflatable curtain 101 is in the sealing position, as discussed further below, the outer wall 102 isolates the internal space 106 from the gas section 6. The inner wall 104 isolates the internal space 106 from the enclosed service space 108.

The inflatable curtain 101 is adapted to receive compressed gas, such as air or biogas, within the internal space 106. The control system 117 connects the internal space 106 to a compressed gas source 128. As shown in FIGS. 6 and 7, the control system 117 includes an inlet line 122 that provides fluid communication between the compressed gas source 128 and the internal space 106. The inlet line 122 includes an inlet solenoid 126 that controls the flow of compressed gas through the inlet line 122. The inlet solenoid 126 can actuate between an open and a closed position. When the inlet solenoid 126 is open, flow is provided through the inlet line 122 from the compressed gas source 128 into the internal space 106. When the inlet solenoid 126 is closed, there is no flow past the inlet solenoid 126.

The control system 117 also includes an outlet line 124. The outlet line 124 provides fluid communication between the internal space 106 and an opening 134 to the outside of the fermenter tank 4. The outlet line 124 includes an outlet solenoid 132 that can actuate between an open and a closed state to control the flow of compressed gas through the outlet line 124.

The inflatable curtain 101 may be lifted by one or more retention springs 118 shown in FIG. 8. The retention springs 118 are extension springs that are attached to the bottom edge of the inflatable curtain 101. The retention springs 118 bias the inflatable curtain 101 to the inoperative position, and hold the inflatable curtain 101 in that position against its weight when the inflatable curtain 101 is not filled with compressed air. Optionally, the retention springs 118 may be replaced by another mechanism that lifts the inflatable curtain 101 when it is not full of compressed air. The lifting mechanism may be biased towards the inoperative position or may move to the inoperative position on command.

The second servicing device 100 can be moved to the sealing position, as shown in FIG. 7, by inflating the inflatable curtain 101. To inflate the inflatable curtain 101, the inlet solenoid 126 is opened and the outlet solenoid 132 is closed. Compressed air or biogas flows from the compressed gas source 128 through the inlet line 122 and into the internal space 106. The compressed gas increases the volume of the internal space 106. The creases 116 accommodate the increased volume by allowing the inflatable curtain 101 to extend towards the fermentation section 5. During inflation, the compressed gas causes the inflatable curtain 101 to extend against the biasing force of the retention springs 118. The extension of the outer and inner walls 102, 104 causes the bottom of the inflatable curtain 101 to enter the fermentation section 5. Webs 138 prevent the outer and inner walls 102, 104 from being blown apart. The webs 138 may be open, or mesh-like, structures as shown. Optionally, a grid of webs 138 may be provided. Alternatively, the webs 138 may be solid and be configured to provide multiple closed compartments, or pockets, connected at one end to other compartments or provided with openings or passages through them such that the compressed gas can reach all of the compartments. The webs 138 may also be provided by lines of stitching holding the outer and inner walls 102, 104 together along various lines of contact. For example, as an alternative to the creases 116 shown in FIG. 8, the outer and inner walls can be stitched together by a set of parallel vertical lines of stitching ending several centimeters from the top of the inflatable curtain 101. This forms a set of vertical, tubular sub-pockets connected to a horizontal header within a larger pocket defined by each wall of the inflatable curtain 101. Optionally, horizontal or diagonal pockets may be provided in addition to or in place of the vertical pockets to help the walls of the inflatable curtain resist bending, to help push the lower edge of the inflatable curtain 101 downwards, or both.

When the inflatable curtain 101 enters to the desired depth of the fermentation section 5, the inlet solenoid 126 can be closed to hold the volume of air or biogas within the internal space 106. This is the sealing position of the second servicing device 100. While in the sealing position, a seal is formed between the surface of the fermentation section 5 and the inflatable curtain 101. This seal isolates the enclosed service space 108 and the service section 112 from the gas section 6.

When the inflatable curtain 101 is in the sealing position, a hatch in the servicing section 112 may be opened to allow biogas in the enclosed service space 108 to be vented, or to be drawn or blown out. With the hatch open and the enclosed service space 108 cleared of biogas, the agitator 23 is accessible for maintenance. For example, the agitator 23 can be raised along the holding rod 26, through the enclosed service space 108, until it is located in the servicing section 112.

Venting the enclosed service space 108 through the hatch of the service section 112 causes a differential pressure to develop across the inflatable curtain 101. The pressure of the biogas within the gas section 6 can be in the range of about 10 to 15, or 12 to 14, inches of water column higher than the atmospheric pressure within the enclosed service space 108. While in the sealing position, the inflatable curtain 101 can withstand this differential pressure and prevent the loss of the produced biogas within the gas section 6 to the atmosphere outside of the fermenter tank 4.

To move the second servicing device 100 to the inoperative position, after closing the hatch in the service section 112, the operator moves the outlet solenoid 132 to an open position and the volume of air or biogas within the internal space 106 vents to outside 134 the fermenter tank 4. This venting allows the retention springs 118 to lift the inflatable curtain 101 to the inoperative position.

Optionally, the retention springs 118 can be pneumatically sprung re-coiling pistons or mechanical springs. Further optionally, the retention springs 118 may be replaced by a crank mechanism 33 as described in relation to FIGS. 1 to 5. The retention springs may also be replaced by pneumatic or hydraulic pistons, or a mechanical actuator, that can be actuated to move the inflatable curtain 101 to both the inoperative position and the sealing position. In this case, the pistons or actuators may also help hold the bottom of the inflatable curtain 101 down in the sealing position, as will be described in more detail in relation to FIGS. 10 to 12. Optionally, an internal supporting structure, as will be described in relation to FIG. 12, may also be added inside of the inflatable curtain 101. When the inflatable curtain 101 is in the inoperative position, biogas can be removed from the gas section 6 through the stack in the top of the service section 112.

Optionally, the inlet line 122 may have a pressure sensor 136. The pressure sensor measures the pressure within the inlet line 122, which provides an indirect measure of the pressure within the internal space 106 when the outlet solenoid is closed. The pressure sensor 136 can be connected to a switch (not shown) so that when a predetermined pressure is reached in the internal space 106, the switch will cause the inlet solenoid 126 to close. Optionally, the predetermined pressure is set to a value with the range of about 10 to 50 p.s.i or 20-30 psi. The pressure sensor 136 can also be used to indicate a need to add more compressed air over time if there is some leakage through the inflatable curtain 101.

Figure 9:
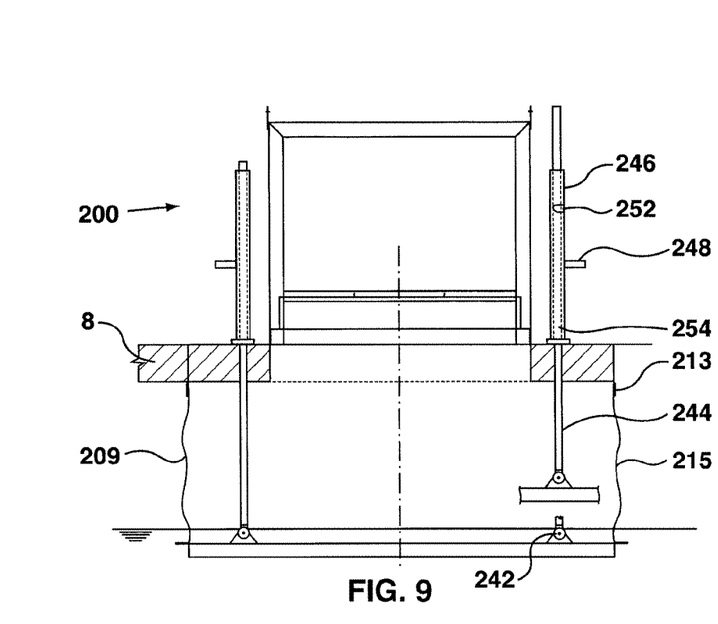
FIG. 9 is a front view of a third service device.
Figure 10:
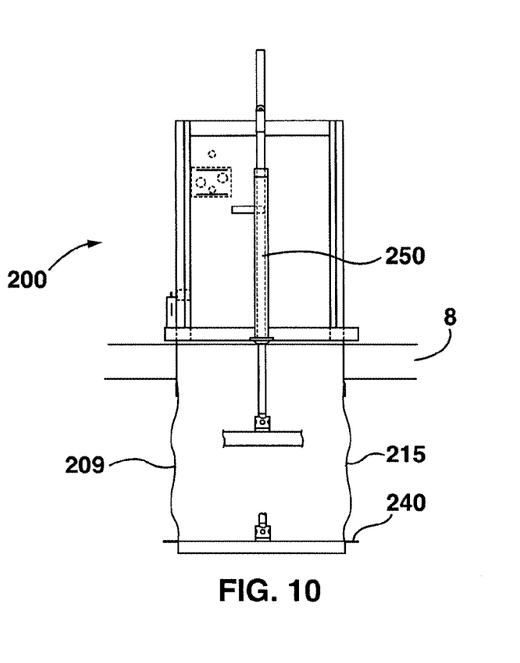
FIG. 10 is a side view of the third service device of FIG. 9.
Figure 11:
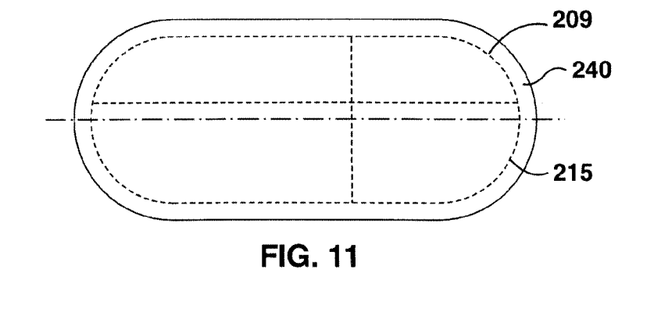
FIG. 11 is a partial bottom view of the third service device of FIG. 9.

FIGS. 9 to 11 show a third servicing device 200 having a third sealing device 209. The third servicing device 200 is generally similar to the servicing device 2 of FIGS. 1 to 5 except in the way that a third retention wall 215 is raised and lowered. When the third retention wall 215 is raised, biogas can be removed from the gas section through a port in the top of the third servicing device 200.

The third retention wall 215 is a flexible membrane attached to a third attachment frame 213 and a lower frame 240. The lower frame 240 provides rigid support to the bottom of the third retention wall 215. The lower frame 240 also provides connection points 242 for an arm 244 that is used to raise and lower the lower frame 240. The arm 244 moves upwards and downwards in a cylinder 246 mounted to the tank cover 8 or to a part of the third servicing device 200. A handle 248 attached to the arm 244 may be used to lift and lower the lower frame 240. The handle 248 travels in a slot 250 in the cylinder between an upper catch 252 or a lower catch 254. Rotating the arm 244 and handle 248 into either catch 252, 254 holds the lower frame 240 in the corresponding position. The lower catch 254 may be located relative to the dimensions of the second sealing device 209 such that the second sealing device 209 is prevented from deflecting inwards by a distance that would interfere with withdrawing the agitator device 23. Optionally, the third sealing device 209 may be inflatable to increase its resistance to bending or an internal supporting structure may be provided within it, or both.

Figure 12:
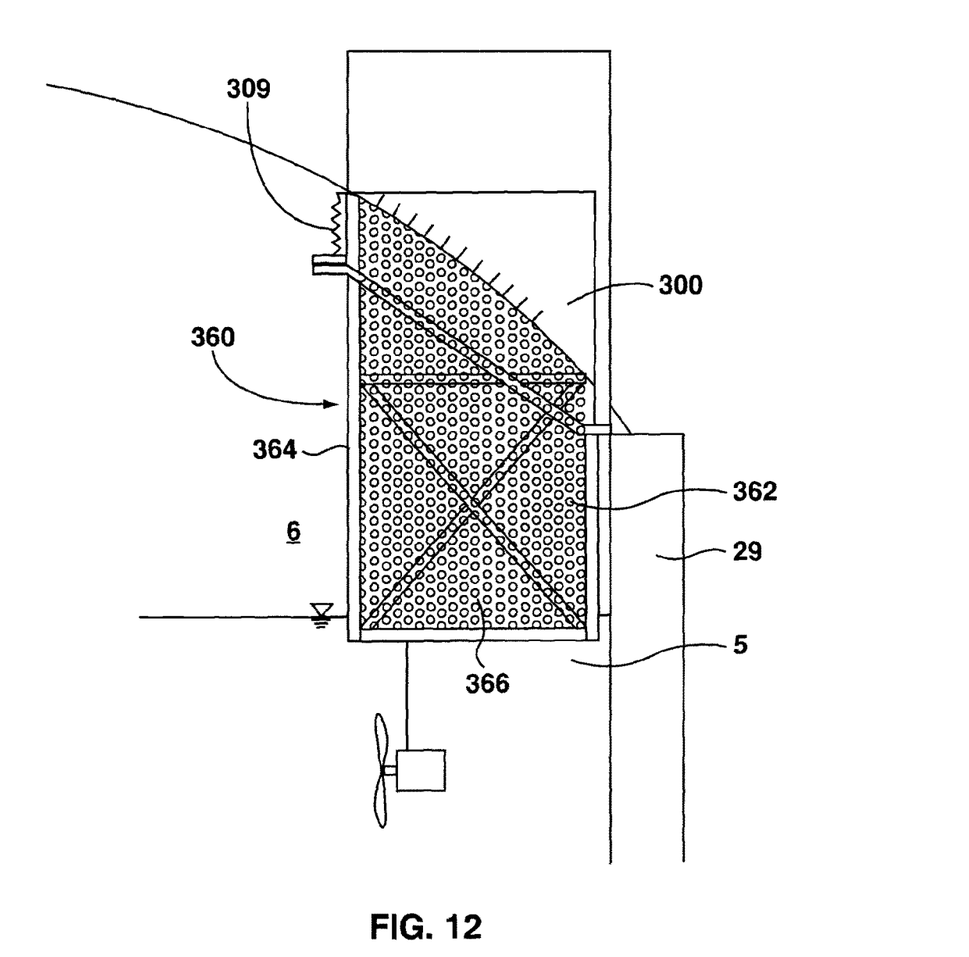
FIG. 12 is a side view of a fourth service device.

FIG. 12 shows a fourth servicing device 300 having a fourth sealing device 309. The further servicing device 300 is generally similar to any of the previously described servicing devices but for the addition of a supporting cage 360 inside of the fourth sealing device 309. The fourth sealing device 309 may be similar to any of the previously described sealing devices. However, if the fourth sealing device 309 is like the sealing device 9 of FIGS. 1 to 5, it is preferably fitted with a weighted lower frame (similar to frame 240 of FIGS. 9 to 11) to help it lower and remain submerged in the fermentation section 5 in the sealing position.

The supporting cage 360 is suspended from the fourth servicing device 300 inside of the fourth sealing device 309. When the fourth sealing device 309 is raised in the inoperative position (as shown in FIG. 12), gas in the gas section 6 is free to move through openings 362 in the supporting cage 360 and can be withdrawn form a port in the fourth servicing device 300. When the fourth sealing device 309 is lowered in the sealing position, the supporting cage 309 helps the fourth sealing device 309 resist the differential pressure between the gas section 6 and the atmosphere.

The supporting cage 360 may be made of various constructions that are rigid yet provide openings 362. In the example show in FIG. 12, the supporting cage 360 has a frame 364 made, for example, of hollow tube or angle sections of stainless steel or aluminum. Optionally, the supporting cage 360 may help support the fourth servicing device 300 on the tank wall 29. The frame 364 is covered by plates 366 with openings 362. For example, the openings 362 may be perforated into the plate 366 or the plate 366 maybe in the form of a screen or grating. The weight of the supporting cage 360 is preferably low and the total area of the openings 362 is preferably high.

The supporting cage 360 is preferably not immersed in the fermentation section 5. Instead, the supporting cage 360 preferably clears the top of the fermentation section 5 by a gap, for example of about 5 cm. The weighted frame mentioned above may be used to help the bottom of the fourth sealing device 309 resist being deflected into this gap.

Figure 13:
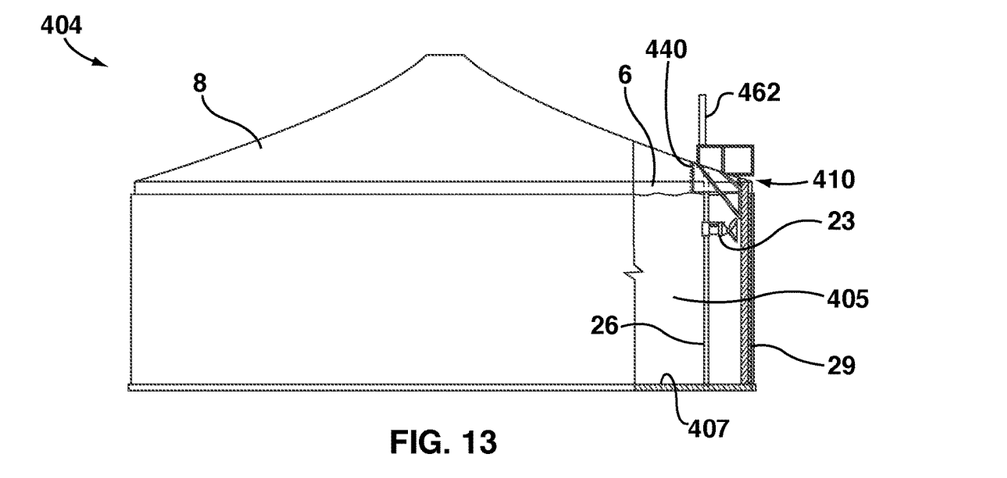
FIG. 13 is a partial cutaway side view of a digester tank with a fifth service device.

FIGS. 13 to 19 show a fifth service device 410 for use with a digester tank 404. FIG. 13 shows a side view of the digester tank 404, which comprises a tank bottom 407, a tank cover 8 and a tank wall 29. The tank cover 8 may be composed of a flexible or non-flexible material. The tank cover 8 is sealed to the tank wall 29 in an essentially gas-tight manner to prevent the escape of biogas.

Figure 14:
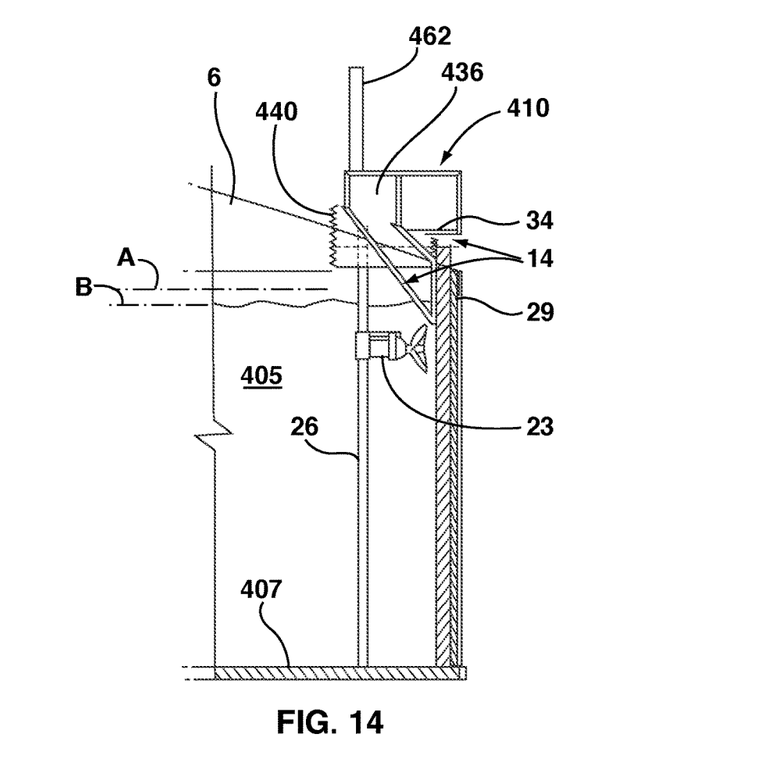
FIG. 14 is an enlarged view of the fifth service device and a portion of the digester tank of FIG. 13.

FIG. 14 shows a body of liquid contents 405 extending upwards from the tank bottom 7. The liquid contents 405 and any solids therein may be digested and contribute to the production of biogas. The biogas may be collected in a plenum, referred to as a gas section 6, between the liquid contents 405 and the tank cover 8.

To promote digestion, the liquid contents 405 may be mixed by at least one agitator 23, which is secured on a holding rod 26. The holding rod 26 may extend from the tank bottom 407 into the gas section 6, possibly to, or past, the tank cover 8. The agitator 23 may move along the holding rod 26, for example, the agitator device 23 may be selectively positioned within or above the liquid contents 405.

The digester tank 404 is provided with one or more fifth service devices 410. The fifth service device 410, as depicted in FIG. 14, is supported by a carrying console 14 on the tank wall 29. The carrying console 14 may be secured on the inside, outside or top of the tank wall 29 or on the adjacent ground.

The fifth service device 410 may be connected directly with the tank cover 8 so as to be gas-tight. Alternatively, various suitable seals may be employed to provide a seal between the fifth servicing device 410 and the tank cover 8.

FIGS. 15 to 19 provide detailed views of the fifth service device 410, which comprises a servicing section 436, a separation curtain 440, a vent pipe 442, an isolation valve 444, a purge valve 446 and a vent valve 448. The fifth service device 410 may also include a platform 34, if it is used with a domed or flexible cover 8 as shown in FIGS. 13 and 14. In FIGS. 15 to 19, a flat concrete cover 8 is used and a platform 34 is not required.

Figure 15:
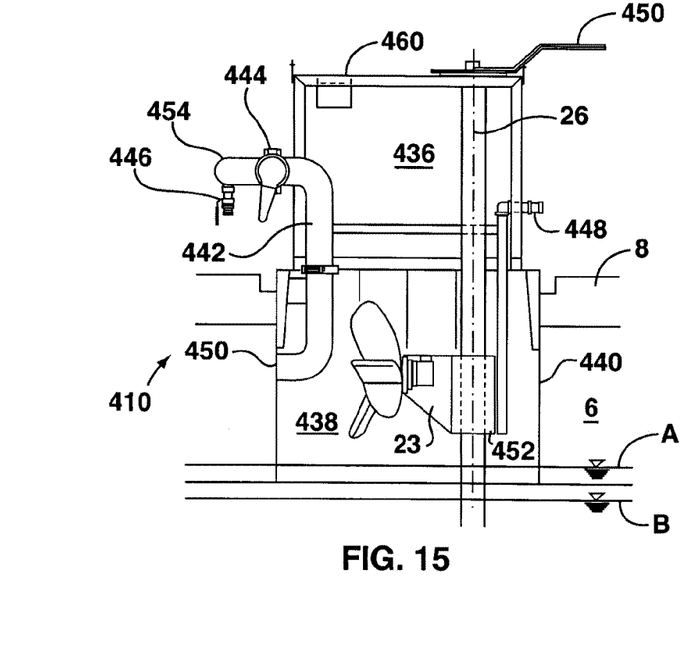
FIG. 15 is a side view of the fifth service device.

The servicing section 36 may form an enclosure, for example a box, with an open bottom that is open to the inside of the digester tank 404. FIG. 15 shows the servicing section 436 above the level of the tank cover 8. The servicing section 436, however, may also be positioned at least partially below the level of the tank cover 8.

The servicing section 436 may include an access port (not shown), which when closed, provides a seal to prevent the loss of gas from the gas section 6 to outside the digester tank 404. When open, the access port allows a user to access the interior of the servicing section 436.

As shown in FIG. 15, the holding rod 26 extends through the open floor of the servicing section 436 so the agitator 23 may be moved into the interior of the servicing section 436. The bottom of the holding rod 26 is attached to the tank bottom 407. The top of the holding rod 26 is held by the servicing section 436. A handle 450 is connected to the holding rod 26 through an upper wall of the servicing section 436 and can be used to rotate the holding rod 26. The agitator 23 rotates with the holding rod 26. The holding rod 26 preferably has a rectangular cross section. The agitator 23 has a set of rollers 452 that allow it to be rolled upwards or downwards on the holding rod 26.

The separation curtain 440 extends downwards from the bottom of the servicing section 436 into the gas section 6 of the digester tank 404 and towards the surface of the liquid contents 405 shown as dotted lines A or B on FIGS. 14 and 15. The separation curtain 440 may have fixed solid walls and an open top and bottom to define an agitator shaft 438 within the separation curtain 440. The separation curtain 440 may be cylindrical, rectangular, square, or any other suitable shape that is of sufficient dimensions to allow the movement of the agitator device 23 along the holding rod 26 within the agitator shaft 38. The top of the separation curtain 440 is adjacent to, and open to, the open bottom of the servicing section 436. The bottom of the separation curtain 440 does not necessarily extend so far as to enter the liquid contents 405 when the agitator 23 is not being serviced. For example, the bottom of the separation curtain 440 may be between 0.5 to 10 inches (1.2 to 25 cm) above the surface of the liquid contents 405 defined by line B. The bottom of the separation curtain 440 does not move relative to the tank bottom 407. As will be discussed further below, the surface of the liquid contents 405 may be raised or maintained at least at the same level as the bottom of the separation curtain 440, for example at line A, to form a seal with the separation curtain 440 when servicing is required.

In normal operation, isolation valve 444 is open. Biogas can be withdrawn from the gas section 6 through the vent pipe 442 and into the servicing section 436. From there, the biogas is withdrawn through a port 460 in the fifth servicing device 410 and a stack 462. If the liquid contents 405 are optionally below the separation curtain 440, biogas can also enter the servicing section 436 by flowing underneath the bottom edge of the separation curtain 440. In this case, the separation curtain 440 also does not interfere with mixing the liquid contents 405. This is advantageous, but the digester 404 can also function with the liquid contents 405 left above the level of the bottom of the separation curtain 440. While an agitator 23 is being serviced, the surface of the liquid contents 405 is at or above the bottom of the separation curtain 440 and the isolation valve 444 is closed. However, another fifth servicing device 410 in the same digester tank 404 can still be used to withdraw biogas by leaving its isolation valve 444 open.

The separation curtain 440 may be made of steel, preferably stainless steel, aluminum, or other composite or non-composite materials that are able to withstand the differential pressures that may develop between the agitator shaft 438 and the gas section 6. The separation curtain 440 may be of a unitary or a modular construction with any joint surfaces sealed, for example welded, caulked or otherwise joined, to prevent fluid communication through the joint surfaces.

The vent pipe 442 has a first end 450 and a second end 452. The first end 450 defines an opening through the separation curtain 440. As depicted in FIG. 15, the vent pipe 442 extends upwards through the agitator shaft 438 into the servicing section 436. In this way, the vent pipe 442 does not require a separate opening in the tank cover 8.

The vent pipe 442 exits though a wall of the servicing section 436 so that a section of the vent pipe 442, referred to as the exterior vent pipe section 454, is outside of the servicing section 436. The exterior vent pipe section 454 re-enters the servicing section 436 at the second end 452 to define another opening through the wall of the servicing section 436. The vent pipe 442 provides fluid communication between the gas section 6 and the servicing section 436. The isolation valve 444 is provided in the exterior vent pipe section 454 so that it is accessible from outside of the servicing section 436.

Optionally, the vent pipe 442 does not extend upwards through the agitator shaft 438, rather the vent pipe 442 may directly exit the digester tank 404, through the tank cover 408. In this case, the exterior vent pipe section 454 extends from the tank cover 8 to the servicing section 436 and the second end 452 defines an opening through the wall of the servicing section 436. However, this requires sealing the vent pipe 442 to the tank cover 8 so it is preferable for the vent pipe 442 to pass through the elevation of the tank cover 8 inside of the fifth servicing device 410.

Figure 16:
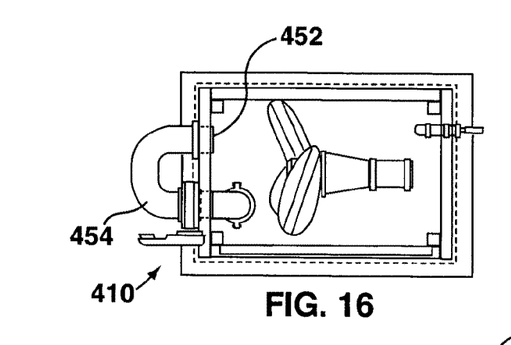
FIG. 16 is a top view of the fifth service device with a top portion removed.
Figure 17:
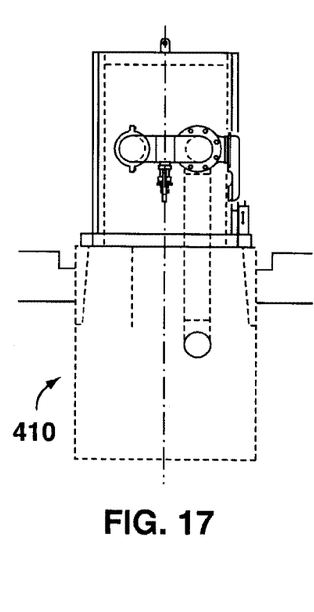
FIG. 17 is a left side view of the fifth service device.
Figure 18:
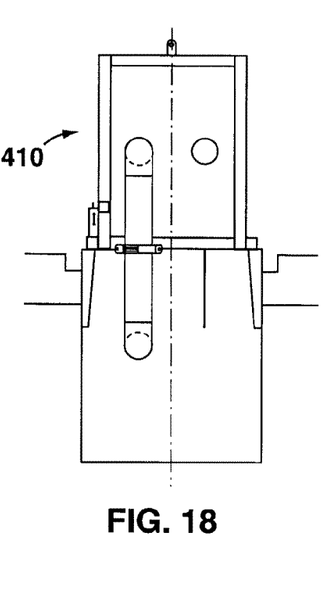
FIG. 18 is a right side view of the fifth service device.
Figure 19:
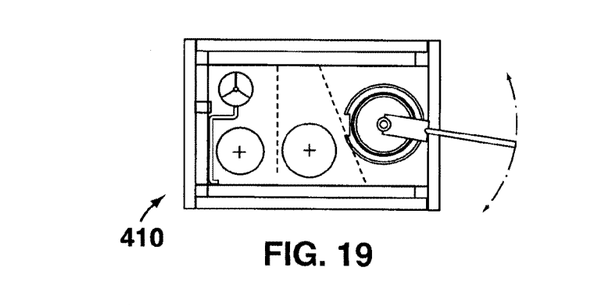
FIG. 19 is a top view of the fifth service device with the top portion in place.

The flow of gas through the vent pipe 442 and, therefore, the flow of gas between the gas section 6 and the servicing section 436, may be regulated by the isolation valve 444. The isolation valve 444 can be a quarter-turn valve, such as a butterfly valve, or other suitable valve that can be closed to form a seal within the vent pipe 442. Closing the isolation valve 444 stops gas flow through the vent pipe 442 and opening the isolation valve 444 allows the flow of gas. The isolation valve 444 is able to withstand any differential pressure that may arise when the isolation valve 444 is closed. FIGS. 15 and 16 depict the isolation valve 444 located on the exterior vent pipe section 454, but the isolation valve 444 may optionally be located elsewhere along the length of the vent pipe 442 provided that it can be actuated from outside of the fifth servicing device 410.

The purge valve 446 may be located in a purge line connected to the exterior vent pipe section 454, as shown in FIGS. 15 and 16. Preferably, the purge valve 446 is located between the isolation valve 444 and the second end 452 and is opened when the isolation valve 444 is closed. Opening the purge valve 446 provides fluid communication between the vent pipe 442, the servicing section 436, the agitator shaft 438, and the atmosphere outside the digester tank 404. Optionally, the purge valve 446 may be located in a line through the wall of the servicing section 436. The purge valve line may be connected to a source of suction or other means (not shown) to help drive gas to outside of the digester tank 404.

The vent valve 448 may be located in a vent line passing through a wall of the servicing section 436. Preferably, the vent valve 448 is located opposite to the second end 452 and the vent line extends downwards inside of the agitator shaft 438. In this way, fresh air drawn in through the vent line displaces biogas in the bottom of the agitator shaft 438. The vent valve 448 provides fluid communication between the outside of the digester tank 404 and the interior of the servicing section 436 and agitator shaft 438. The vent line may be connected to a blower or other means to drive gas from the interior of the servicing section 436 and agitator shaft 438 to outside the digester tank 404.

In operation, the surface of the liquid contents 405 may be raised to form a seal at, or near, the bottom of the separation curtain 440 and the isolation valve 444 can be closed to isolate the servicing section 436 from the gas section 6. The term "isolate" refers to a decreased, or lack of, gas communication from the gas section 6 to the agitator shaft 438 and the servicing section 436, and vice versa. The isolated servicing section 436 remains in fluid communication with the portion of the agitator shaft 438 that is above the surface of the liquid contents 405. Further, the movement of the agitator 23 through the agitator shaft 438 is not hindered by the isolation of the servicing section 436.

The surface of the liquid contents 405 may be raised to the level of the separation curtain 440 to allow servicing by various methods. For example, the volume of the liquid contents 405 may be increased by the addition of further liquid contents 405, by increasing the rate of feeding liquid contents 405, or by decreasing the rate of draining liquid contents 405. The increased volume causes the surface of the liquid contents 405 to rise towards the bottom of the separation curtain 440. Alternatively, a displacement member (not shown) may be retractably submerged within, and cause displacement of, the liquid contents 405. This displacement causes the surface of the liquid contents 405 to rise towards the separation curtain 440. When the surface of the liquid contents 405 rises to reach at least the bottom of the separation curtain 440, a seal is formed across the agitator shaft 438 that prevents further fluid communication from the gas section 6 through the bottom of the separation curtain 440.

Before, during or after the seal is formed at the bottom of the separation curtain 440, the isolation valve 444 is closed to stop the flow of gas from the gas section 6 to the servicing section 436 through the vent pipe 442. Closing the isolation valve 444 and forming the seal at the bottom of the separation curtain 440 isolates the agitator shaft 438 and the servicing section 436 from the gas section 6.

When the agitator shaft 438 and servicing section 436 are isolated, the purge valve 446 and vent valve 448 may be opened to purge the volume of biogas from within the agitator shaft 438, the servicing section 436, and the part of the vent pipe 442 that is between the isolation valve 444 and the second end 452. This purged biogas is purged to outside of the digester tank 404. Optionally, a blower or vacuum may be used to assist with purging the biogas. As a further option, the purged biogas may be collected and re-directed into the gas section 6.

The vent valve 448 may be opened to allow air from outside the digester tank 404 to flow into the servicing section 436 to replace the purged biogas. When the purged biogas has been replaced, the purge valve 446 and the vent valve 448 may be closed.

With the gas section 6 isolated from the servicing section 436, the operator may open the access port to access the interior of the servicing section 436 with a minimal loss of the gas contents of the gas section 6. The agitator 23 may be moved along the holding rod 26, through the agitator shaft 438, and held in the servicing section 436 to a person to access to the agitator 23 to inspect or service the agitator 23. The movement of the agitator 23 into the servicing section 436 may occur before, during or after the isolation of the servicing section 436.

When the inspection or maintenance procedure is complete, the access port is closed. The purge valve 446 and the vent valve 448 are also closed, if they are not closed already, and the isolation valve 444 is opened to re-establish gas flow between the gas section 6 and the servicing section 436. One or both of the purge valve 446 and the vent valve 448 may be briefly left open to allow the non-biogas gas to leave the service section 436 and the agitator shaft 438.

The surface of the liquid contents 405 may be lowered to remove the seal at the separation curtain 440 by reducing the volume of the liquid contents 405 or retracting the displacement member from within the liquid contents 405. The agitator 23 may be lowered through the agitator shaft 438 to resume agitation or mixing of the liquid contents 405.

We claim:

1. A service device for use with a digester tank that contains a liquid and defines a gas section under a cover, the service device comprising:
   a) a service section sealed to the cover;
   b) a separation curtain extending downwards from the service section; and,
   c) a conduit to provide fluid communication between the service section and the gas section; and
   d) an isolation valve in the conduit.

2. The service device of claim 1 wherein the conduit extends upwards through the elevation of the cover inside of the service device.

3. The service device of claim 1 having a vent valve and a purge valve.

4. The service device of claim 1 having a first port in the service section for withdrawing biogas from the gas section through the service section.

5. The service device of claim 1 further comprising a hatch that allows access to the inside of the tank from outside of the service device.

6. The service device of claim 1 wherein the separation curtain comprises an opening, and the conduit extends inwards from the opening in the separation curtain and then upwards within the service device.

7. The service device of claim 6 wherein, once above the cover, the conduit exits through a wall of the service device and then returns to the service device through a second port in the service device.

8. The service device of claim 1 wherein the isolation valve is located outside of the service device and above the cover.

9. The service device of claim 1 further comprising a purge line with a valve and a vent with a valve.

10. The service device of claim 1 wherein the separation curtain is fixed.

11. A combination of a service device according to claim 1 and a digester wherein the service device is supported on the tank or on the ground near the tank, the outside of the service device is sealed to a cover of the tank, the inside of the service device can be put in fluid communication with a gas section of the tank or separated from the gas section of the tank, and a hatch in the service device allows access to the inside of the tank from outside of the service device.

12. The combination of claim 11 wherein the service device includes a fixed separation curtain which extends downwards from a tank cover towards the liquid contents of a tank.

13. The combination of claim 12 wherein the servicing device also includes a pipe that provides fluid communication between the gas section and the inside of the servicing device.

14. The combination of claim 13 wherein the pipe can be selectively closed to prevent the communication.

15. The combination of claim 13 wherein the pipe extends inwards from a port in the separation curtain and then upwards within the service device.

16. The combination of claim 15 wherein, once above the cover, the pipe passes through a wall of the service device and then returns to a port in the service device.

17. The combination of claim 16 wherein a shut off valve is located in the portion of pipe outside of the service device and above the cover.

18. The combination of claim 12 wherein the service device has a purge line with a valve and a vent with a valve.

19. The combination of claim 11 wherein the service device has a biogas outlet.

20. The combination of claim 11 wherein the digester has two or more service devices.

21. A method of operating a digester with a service device according to claim 1 having a fixed separation curtain wherein the surface of the liquid contents is made high enough, at least when servicing is required, to form a seal with the bottom of the separation curtain.

22. The method of claim 21 further comprising a step of closing a vent pipe to isolate the gas section from the inside of the service device.

23. The method of claim 21 further comprising purging the service device of biogas.

24. The method of claim 21 wherein in a digester with more than one service device, biogas is withdrawn from a second service device while a first service device is isolated by leaving the pipe of the second device open.

25. The method of claim 21 wherein, after inspecting or servicing the digester, the liquid contents may be lowered or allowed to drop to below the bottom of the separation curtain.

26. A method for servicing a digester tank comprising a cover and containing a liquid and a gas, the method comprising the steps of:
   a) providing a service device according to claim 1;

b) raising the surface of the liquid to form a seal between the separation curtain and the gas; and, c) opening a hatch between the outside of the digester tank and the separation curtain.

27. The method of claim 26 wherein the digester comprises a second separation curtain and wherein the method comprises a step of withdrawing biogas through the second separation curtain after raising the surface of the liquid.

28. The method of claim 27 wherein biogas is withdrawn through an opening in side wall of the second separation curtain.

29. The method of claim 26 comprising closing an opening in the side of the separation curtain.

* * * * *